US010219515B2

(12) United States Patent
Mecfel-Marczewski et al.

(10) Patent No.: US 10,219,515 B2
(45) Date of Patent: Mar. 5, 2019

(54) AGROCHEMICAL ADJUVANT CONTAINING 2-OXO-1,3-DIOXOLAN-4 CARBOXYLATES

(71) Applicant: BASF SE, Ludwigshafen (DE)

(72) Inventors: Joanna Mecfel-Marczewski, Limburgerhof (DE); Matthias Krejca, Plauen (DE); Diana Franz, Schifferstadt (DE); Matthias Bratz, Maxdorf (DE); Rainer Berghaus, Speyer (DE); Diana Westfalia Moran Puente, Nussloch (DE); Sophie Putzien, Ampfing (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/524,759

(22) PCT Filed: Nov. 3, 2015

(86) PCT No.: PCT/EP2015/075581
§ 371 (c)(1),
(2) Date: May 5, 2017

(87) PCT Pub. No.: WO2016/071331
PCT Pub. Date: May 12, 2016

(65) Prior Publication Data
US 2017/0318811 A1  Nov. 9, 2017

(30) Foreign Application Priority Data

Nov. 7, 2014 (EP) .................................. 14192200

(51) Int. Cl.
| *A01N 47/06* | (2006.01) |
|---|---|
| *A01N 37/50* | (2006.01) |
| *A01N 57/20* | (2006.01) |
| *A01N 25/02* | (2006.01) |
| *C07D 325/00* | (2006.01) |

(52) U.S. Cl.
CPC ............. *A01N 47/06* (2013.01); *A01N 25/02* (2013.01); *A01N 37/50* (2013.01); *A01N 57/20* (2013.01); *C07D 325/00* (2013.01)

(58) Field of Classification Search
CPC ........ A01N 25/02; A01N 47/06; A01N 57/20; A01N 37/50; C07D 325/00
See application file for complete search history.

(56) References Cited

U.S. PATENT DOCUMENTS

| 6,307,129 | B1 | 10/2001 | Ward et al. |
|---|---|---|---|
| 7,022,896 | B1 | 4/2006 | Weeks et al. |
| 7,105,724 | B2 | 9/2006 | Weeks et al. |
| 7,381,861 | B2 | 6/2008 | Cerny et al. |
| 7,632,985 | B2 | 12/2009 | Malven et al. |
| 2005/0227872 | A1 | 10/2005 | Volgas et al. |
| 2008/0015110 | A1 | 1/2008 | Clemente et al. |
| 2008/0028482 | A1 | 1/2008 | Beazley et al. |
| 2009/0029891 | A1 | 1/2009 | Callahan |
| 2013/0085209 | A1* | 4/2013 | Klopsch ............... C08K 5/1565 523/455 |
| 2014/0227366 | A1* | 8/2014 | Zindel .................... A01N 25/10 424/604 |

FOREIGN PATENT DOCUMENTS

| EP | 0 374753 | 6/1990 | |
|---|---|---|---|
| EP | 0 392 225 | 10/1990 | |
| EP | 0 427 529 | 5/1991 | |
| EP | 0 451 878 | 10/1991 | |
| WO | WO-95/34656 | 12/1995 | |
| WO | WO-99/29170 | 6/1999 | |
| WO | WO-02/015701 | 2/2002 | |
| WO | WO-02/078441 | 10/2002 | |
| WO | WO-03/018810 | 3/2003 | |
| WO | WO-03/052073 | 6/2003 | |
| WO | WO-2007/143690 | 12/2007 | |
| WO | WO-2010/080829 | 7/2010 | |
| WO | WO-2011/157551 | 12/2011 | |
| WO | WO-2011157551 A1 * | 12/2011 | ........... C07D 317/34 |
| WO | WO-2012/010467 | 1/2012 | |
| WO | WO-2013034513 A2 * | 3/2013 | ............. A01N 25/04 |
| WO | WO-2013/153030 | 10/2013 | |
| WO | WO-2014/057064 | 4/2014 | |

(Continued)

OTHER PUBLICATIONS

European Search Report dated Mar. 20, 2015 for EP Application No. 14192200.5.
International Search Report dated Dec. 9, 2015 for PCT/EP2015/075581.
International Preliminary Report on Patentability dated May 18, 2017 for PCT/EP2015/075581.
Arias et al., "Molecular Evolution of Herbicide Resistance to Phytoene Desaturase Inhibitors in Hydrilla Verticillata and its Potential Use to Generate Herbicide-Resistant Crops," Pest Management Science, 2005, vol. 61, Issue 3, pp. 258-268.

(Continued)

*Primary Examiner* — Sarah Pihonak

(74) *Attorney, Agent, or Firm* — Brinks Gilson & Lione

(57) ABSTRACT

The present invention relates to a method for preparing a tank mix, which comprises the step of contacting a pesticide formulation, water, and a tank mix adjuvant which comprises a carbonate of the formula (I); to a pesticide formulation comprising the tank mix adjuvant; to a method of controlling phytopathogenic fungi and/or undesired vegetation and/or undesired insect or mite attack and/or for regulating the growth of plants, wherein the tank mix or the pesticide formulation is allowed to act on the respective pests, their environment or the plants to be protected from the respective pest, on the soil and/or on undesired plants and/or the crop plants and/or their environment; and to a use of the tank mix adjuvant for increasing the efficacyl of a pesticide.

12 Claims, No Drawings

(56) References Cited

FOREIGN PATENT DOCUMENTS

| WO | WO-2014/118268 | 8/2014 |
|----|----------------|--------|
| WO | WO-2014/145232 | 9/2014 |

OTHER PUBLICATIONS

Behrens et al., "Dicamba Resistance: Enlarging and Preserving Biotechnology-Based Weed Management Strategies," Science, 2007, vol. 316, Issue 5828, pp. 1185-1188.

Curran et al., "Agronomy Facts 37: Adjuvants for Enhancing Herbicide Performance," 2009, pp. 1-6, retrieved from internet on Mar. 11, 2015. (http://extension.psu.edu/pests/weeds/control/adjuvants-for-enhancing-herbicide-performance).

Dill et al., "Glyphosate-Resistant Crops: Adoption, Use and Future Considerations," Pest Management Science, 2008, vol. 64, Issue 4, pp. 326-331.

Green et al., "New Multiple-Herbicide Crop Resistance and Formulation Technology to Augment the Utility of Glyphosate," Pest Management Science, 2008, vol. 64, Issue 4, pp. 332-339.

Green, "Evolution of Glyphosate-Resistant Crop Technology," Weed Science, 2009, vol. 57, Issue 1, pp. 108-117.

Harell et al., "Scales 2: Computer Program to Convert Among Developmental Stage Scales for Corn and Small Grains," Agronomy Journal, 1998, vol. 90, Issue 2, pp. 235-238.

Inui et al., "Herbicide Resistance in Transgenic Plants with Mammalian P450 Monooxygenase Genes," Pest Management Science, 2005, vol. 61, Issue 3, pp. 286-291.

Li et al., "Development of PPO Inhibitor-Resistant Cultures and Crops," Pest Management Science, 2005, vol. 61, Issue 3, pp. 277-285.

Matringe et al., "p-Hydroxyphenylpyruvate Dioxygenase Inhibitor-Resistant Plants," Pest Management Science, 2005, vol. 61, Issue 3, pp. 269-276.

Tan et al., "Imidazolinone-Tolerant Crops: History, Current Status and Future," Pest Management Science, 2005, vol. 61, Issue 3, pp. 246-257.

Williams et al., "Differences in Zoospore Germination and Host Penetration in Response to Temperature Among Western Australian Isolates of Plasmopara Viticola," Australian Journal of Agricultural Research, 2007, vol. 58, Issue 7, pp. 703-710.

Chen et al., "Curing of Epoxy Resin Contaminated with Water," *Journal of Applied Polymer Science*, 2001, vol. 79, No. 2, pp. 214-220.

\* cited by examiner

AGROCHEMICAL ADJUVANT CONTAINING 2-OXO-1,3-DIOXOLAN-4 CARBOXYLATES

This application is a National Stage application of International Application No. PCT/EP2015/075581, filed Nov. 3, 2015. This application also claims priority under 35 U.S.C. § 119 to European Patent Application No. 14192200.5, filed Nov. 7, 2014.

The present invention relates to a method for preparing a tank mix, which comprises the step of contacting a pesticide formulation, water, and a tank mix adjuvant, which comprises a carbonate of the formula (I); to a pesticide formulation comprising the tank mix adjuvant; to a method of controlling phytopathogenic fungi, and/or undesired vegetation, and/or undesired insect or mite attack, and/or for regulating the growth of plants, wherein the tank mix or the pesticide formulation is allowed to act on the respective pests, their environment or the plants to be protected from the respective pest, on the soil and/or on undesired plants, and/or the crop plants and/or their environment. The preferred embodiments of the invention mentioned herein below have to be understood as being preferred either independently from each other or in combination with one another.

It is generally known that the uptake and biological efficacy of pesticides may be improved by adjuvants. It is still a goal to develop better adjuvants. It was an object of the present invention to find an adjuvant which is well suited to pesticides. Furthermore, the adjuvant should make possible a storage-stable formulation of the pesticides. Another object was to increase the biological activity of the pesticide formulation. Finally, this adjuvant was to avoid phytotoxic side-effects.

The object was solved by a method for preparing a tank mix, which comprises the step of contacting a pesticide formulation, water, and a tank mix adjuvant which comprises a carbonate of the formula (I)

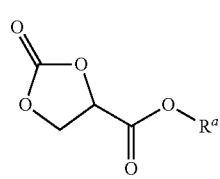
(I)

where $R^a$ is a $C_{1-12}$ alkyl, or a n-valent radical derived by abstraction of the OH groups of an n-valent polyol and which is substituted by n minus 1 carbonate groups of the formula (II)

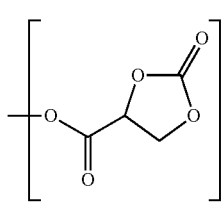
(II)

where n is from 2 to 4 and the polyol is an aliphatic polyol comprising 2 to 10 carbon atoms.

In one form of the invention, $R^a$ is a branched or linear $C_{1-12}$ alkyl, preferably $C_{1-8}$ alkyl, more preferably $C_{1-5}$ alkyl, especially preferably $C_{1-3}$ alkyl, and in particular $C_{1-2}$ alkyl.

$R^a$ may be n-pentyl, iso-pentyl, neo-pentyl, n-butyl, iso-butyl, tert-butyl, n-propyl, sec-propyl, ethyl or methyl, in particular ethyl or methyl, especially methyl.

In another form of the invention, $R^a$ is usually an aliphatic linear or branched n-valent polyol, comprising 2 to 10 carbon atoms, preferably 2 to 8, more preferably 2 to 6, especially preferably 2 to 4, and in particular 2.

The index n usually ranges from 2 to 4, preferably from 2 to 3. In particular, the index n is 2. Typically, the index n ranges from 2 to 3 and the aliphatic polyol comprises from 2 to 10 carbon atoms, preferably from 2 to 8, more preferably from 2 to 6 and especially preferably from 2 to 4. In another typical form, the index n is 2 and the aliphatic polyol comprises from 2 to 10 carbon atoms, preferably from 2 to 8, more preferably from 2 to 6 and especially preferably from 2 to 4.

By one way of example, $R^a$ is ethane-1,2-diol as displayed in formula (a).

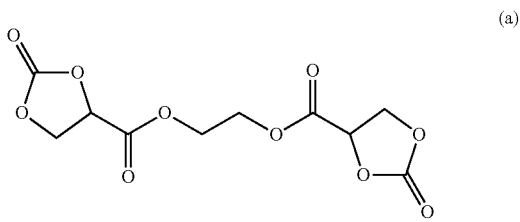 [SMILES: O=C1OCC(C(=O)OCCOC(=O)C2COC(=O)O2)O1]
(a)

By one way of example, $R^a$ is an aliphatic linear or branched 2-valent polyol comprising 4 carbon atoms; in particular $R^a$ is butane-1,4-diol as displayed in formula (b).

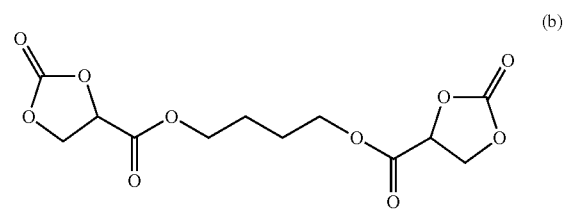 [SMILES: O=C1OCC(C(=O)OCCCCOC(=O)C2COC(=O)O2)O1]
(b)

By another one way of example, $R^a$ is an aliphatic linear or branched 2-valent polyol comprising 5 carbon atoms; in particular $R^a$ is neopentyl glycol as displayed in formula (c).

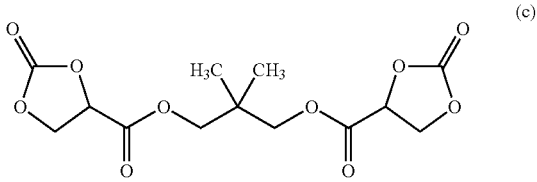 [SMILES: CC(C)(COC(=O)C1COC(=O)O1)COC(=O)C1COC(=O)O1]
(c)

By another one way of example, $R^a$ is an aliphatic linear or branched 3-valent polyol comprising 6 carbon atoms; in particular $R^a$ is 1,1,1-trimethylolpropane as displayed in formula (d).

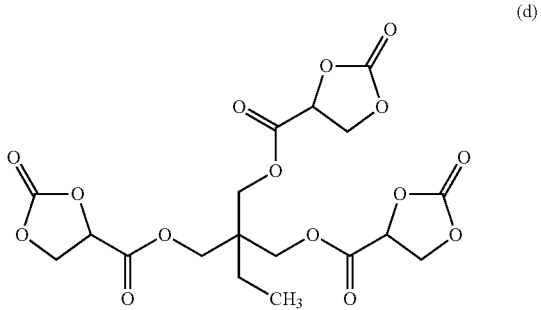 [SMILES: CCC(COC(=O)C1COC(=O)O1)(COC(=O)C1COC(=O)O1)COC(=O)C1COC(=O)O1]

(d)

Typically, $R^a$ is a linear or branched $C_{1-10}$ alkyl, or the index n is 2 or 3 and the aliphatic polyol comprises from 2 to 8 carbon atoms.

In another typical form, $R^a$ is selected from methyl, ethyl, n-butyl, iso-butyl, n-hexyl, branched octyl and branched decyl, or the index n is 2 and the aliphatic polyol is 1,2-ethandiol, 1,4-butandiol or 2,2-dimethyl-1,3-propanediol. In yet another typical form, $R^a$ is methyl, or the index n is 2 and the aliphatic polyol is 1,2-ethandiol.

The preparation of compounds of formulae (I) and (II) can be achieved by chemical synthesis using methods described in literature, e.g. in WO 2011/157551.

The tank mix contains typically from 0.005 to 2.0 wt %, preferably from 0.01 to 1.0 wt %, and in particular from 0.05 to 0.3 wt % of the tank mix adjuvant. In a preferred form the tank mix contains from 0.01 to 1.0 wt % of the tank mix adjuvant.

The step of contacting of the pesticide formulation, water, and the tank mix adjuvant may be achieved by mixing the components in any sequence. The contacting may take place in a tank, in which the tank mix is prepared, by pouring the pesticide formulation, water, and the tank mix adjuvant into the tank, optionally followed by stirring. Preferably, the contacting is done at ambient temperature, such as from 5 to 45° C.

The weight ratio of pesticide formulation to water in the tank mix is usually in a range of from 1:1 to 1:10000, more preferably from 1:5 to 5000, and in particular from 1:10 to 1:1000.

The weight ratio of the pesticide to the carbonate of formula (I) in the tank mix is usually from 10:1 to 1:1000, preferably from 1:1 to 1:100, most preferably from 1:1 to 1:50, and in particular 1:5 to 1:20.

The tank mix is usually an aqueous liquid, which is ready to be applied (e.g. by spraying) in the method of controlling phytopathogenic fungi and/or undesired vegetation and/or undesired insect or mite attack and/or for regulating the growth of plants.

Typically, the tank mix contains at least 50 wt % water, preferably at least 65 wt %, more preferably at least 80 wt % and in particular at least 90 wt %. The water is usually untreated natural water, such as ground water, rain water collected in a water reservoir, river water, or lake water. In another form the water is treated water. For comparison, treated water relates to tap water, which has passed a sewage plant.

The method for preparing the tank mix may comprises the step of contacting a pesticide formulation, water, a tank mix adjuvant, and optionally an auxiliary. The pesticide formulation may also comprise an auxiliary, which may be different or identical to the auxiliary to be added to the tank mix. Examples for auxiliaries are solvents, liquid carriers, solid carriers or fillers, surfactants, dispersants, emulsifiers, wetters, further adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof. Preferred solvents are organic solvents.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.)

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters. Examples of polymeric surfactants are home- or copolymers of vinylpyrrolidone, vinylalcohols, or vinylacetate. Preferred nonionic surfactants are alkoxylates.

Typically, the tank mix adjuvant contains at least 10 g/l, preferably at least 50 g/l, and in particular at least 100 g/l of the non-ionic surfactants. Typically, the tank mix adjuvant contains up to 600 g/l, preferably up to 500 g/l, and in particular up to 400 g/l of the non-ionic surfactants. Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable polyelectrolytes are polyacids or polybases. Examples of polyacids are alkali salts of polyacrylic acid or polyacid comb polymers. Examples of polybases are polyvinylamines or polyethyleneamines.

Suitable further adjuvants are compounds, which have a neglectable or even no pesticidal activity themselves, and which improve the biological performance of the pesticide on the target. Examples of further adjuvants are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids. Preferred anti-foaming agents are silicones, such as polydimethylsiloxan.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

The present invention also relates to the pesticide formulation comprising the tank mix adjuvant. Usually, the pesticide formulation comprises the tank mix adjuvant which comprises the carbonate of the formula (I)

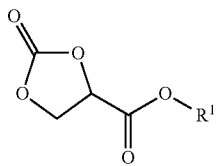

(I)

where $R^1$ is a $C_{1-12}$ alkyl, or a n-valent radical derived by abstraction of the OH groups of an n-valent polyol and which is substituted by n minus 1 carbonate groups of the formula (II)

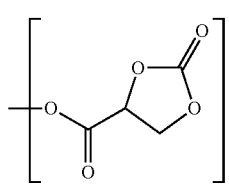

(II)

where n is from 2 to 4 and the polyol is an aliphatic polyol comprising 2 to 10 carbon atoms. In another form the pesticide formulation comprises the carbonate of the formula (I).

The pesticide formulation contains typically from 0.1 to 45 wt %, preferably from 1 to 35 wt %, and in particular 3 to 25 wt % of the tank mix adjuvant. In a preferred form the pesticide formulation contains from 1 to 35 wt % of the tank mix adjuvant. In a preferred form, the tank mix adjuvant consists of the carbonate of the formula (I) and the amount of tank mix adjuvant in the pesticide formulation refers to the of the amount of carbonate of the formula (I).

The weight ratio of the pesticide to the carbonate of formula (I) in the pesticide formulation is usually from 10:1 to 1:1000, preferably from 1:1 to 1:100, most preferably from 1:1 to 1:50, and in particular 1:5 to 1:20.

Pesticide formulations are generally known and commercially available. Pesticide formulations usually comprise a pesticide and an auxiliary. Pesticide formulations may be any type of agrochemical formulation, such as solid or liquid formulations. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), solutions (e.g. SL). Further examples for compositions types are listed in the "Catalogue of pesticide formulation types and international coding system", Technical Monograph No 2, 6th Ed. May 2008, CropLife International. Preferably, the pesticide formulation is an aqueous liquid formulation, such as an SL formulation.

The pesticide formulation may contain at least 3 wt %, preferably at least 10 wt %, and in particular at least 30 wt % of the pesticide. The pesticide formulation may contain up to 60 wt %, preferably up to 50 wt % of the pesticide. In one embodiment, the pesticide formulation contains from 3 to 60 wt % of the pesticide. In another embodiment, the pesticide formulation contains from 10 to 50 wt % of the pesticide.

The pesticide is preferably present in dissolved form in the pesticide formulation. In a more preferred form the pesticide is a water-soluble pesticide and is dissolved in the aqueous phase of the pesticide formulation (e.g. a SL formulation).

It is also possible to use at least one, such as one, two or three different pesticide formulations when preparing the tank mix.

The term "pesticide" within the meaning of the invention states that one or more compounds can be selected from the group consisting of fungicides, insecticides, nematicides, herbicide and/or safener or growth regulator, preferably from the group consisting of fungicides, insecticides or herbicides, most preferably from the group consisting of herbicides. Also mixtures of pesticides of two or more the aforementioned classes can be used. The skilled artisan is familiar with such pesticides, which can be, for example, found in the Pesticide Manual, 15th Ed. (2009), The British Crop Protection Council, London. Suitable insecticides are insecticides from the class of the carbamates, organophosphates, organochlorine insecticides, phenylpyrazoles, pyrethroids, neonicotinoids, spinosins, avermectins, milbemycins, juvenile hormone analogs, alkyl halides, organotin compounds nereistoxin analogs, benzoylureas, diacylhydrazines, METI acarizides, and insecticides such as chloropicrin, pymetrozin, flonicamid, clofentezin, hexythiazox, etoxazole, diafenthiuron, propargite, tetradifon, chlorofenapyr, DNOC, buprofezine, cyromazine, amitraz, hydramethylnon, acequinocyl, fluacrypyrim, rotenone, or their derivatives. Suitable fungicides are fungicides from the classes of dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

The pesticide may be dissolved or dispersed (e.g. suspended) in the tank mix. Preferably, the pesticide is dissolved in the tank mix. The pesticide, such as the auxin herbicide, has often a solubility in water at 20° C. of at least 10 g/l, preferably of at least 50 g/l, and in particular of at least 100 g/l.

In another preferred form the pesticide contains a anionic pesticide. The term "anionic pesticide" refers to a pesticide, which is present as an anion. Preferably, anionic pesticides relate to pesticides comprising a protonizable hydrogen. More preferably, anionic pesticides relate to pesticides comprising a carboxylic, thiocarbonic, sulfonic, sulfinic, thiosulfonic, phosphinic, or phosphorous acid group, especially a carboxylic acid group. The aforementioned groups may be partly present in neutral form including the protonizable hydrogen.

Usually, anions such as anionic pesticides comprise at least one anionic group. Preferably, the anionic pesticide comprises one or two anionic groups. In particular the anionic pesticide comprises exactly one anionic group. An example of an anionic group is a carboxylate group (—C(O)O$^-$). The aforementioned anionic groups may be partly present in neutral form including the protonizable hydrogen. For example, the carboxylate group may be present partly in neutral form of carboxylic acid (—C(O)OH). This is preferably the case in aqueous compositions, in which an equilibrium of carboxylate and carboxylic acid may be present.

Suitable anionic pesticides are given in the following. In case the names refer to a neutral form or a salt of the anionic pesticide, the anionic form of the anionic pesticides are meant. For example, the anionic form of dicamba may be represented by the following formula:

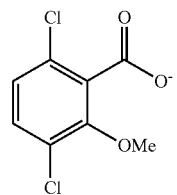 [SMILES: COc1c(Cl)ccc(Cl)c1C(=O)[O-]]

As another example, the anionic form of glyphosate may contain one, two, three, or a mixture thereof, negative charges.

It is known to an expert, that the dissociation of the functional groups and thus the location of the anionic charge may depend for example on the pH, when the anionic pesticides is present in dissolved form. The acid dissociation contants $pK_a$ of glyphosate are typically 0.8 for the first phosphonic acid, 2.3 for the carboxylic acid, 6.0 for the second phosphonic acid, and 11.0 for the amine.

Suitable anionic pesticides are herbicides, which comprise a carboxylic, thiocarbonic, sulfonic, sulfinic, thiosulfonic or phosphorous acid group, especially a carboxylic acid group. Examples are aromatic acid herbicides, phenoxycarboxylic acid herbicides or organophosphorous herbicides comprising a carboxylic acid group.

Suitable aromatic acid herbicides are benzoic acid herbicides, such as diflufenzopyr, naptalam, chloramben, dicamba, 2,3,6-trichlorobenzoic acid (2,3,6-TBA), tricamba; pyrimidinyloxybenzoic acid herbicides, such as bispyribac, pyriminobac; pyrimidinylthiobenzoic acid herbicides, such as pyrithiobac; phthalic acid herbicides, such as chlorthal; picolinic acid herbicides, such as aminopyralid, clopyralid, picloram; quinolinecarboxylic acid herbicides, such as quinclorac, quinmerac; or other aromatic acid herbicides, such as aminocyclopyrachlor. Preferred are benzoic acid herbicides, especially dicamba.

Suitable phenoxycarboxylic acid herbicides are phenoxyacetic herbicides, such as 4-chlorophenoxyacetic acid (4-CPA), (2,4-dichlorophenoxy)acetic acid (2,4-D), (3,4-dichlorophenoxy)acetic acid (3,4-DA), MCPA (4-(4-chloro-o-tolyloxy)butyric acid), MCPA-thioethyl, (2,4,5-trichlorophenoxy)acetic acid (2,4,5-T); phenoxybutyric herbicides, such as 4-CPB, 4-(2,4-dichlorophenoxy)butyric acid (2,4-DB), 4-(3,4-dichlorophenoxy)butyric acid (3,4-DB), 4-(4-chloro-o-tolyloxy)butyric acid (MCPB), 4-(2,4,5-trichlorophenoxy)butyric acid (2,4,5-TB); phenoxypropionic herbicides, such as cloprop, 2-(4-chlorophenoxy)propanoic acid (4-CPP), dichlorprop, dichlorprop-P, 4-(3,4-dichlorophenoxy)butyric acid (3,4-DP), fenoprop, mecoprop, mecoprop-P; aryloxyphenoxypropionic herbicides, such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop. Preferred are phenoxyacetic herbicides, especially 2,4-D.

The term "organophosphorous herbicides" usually refers to herbicides containing a phosphinic or phosphorous acid group. Suitable organophosphorous herbicides comprising a carboxylic acid group are bialafos, glufosinate, glufosinate-P, glyphosate. A preferred organophosphorous herbicide is glyphosate.

Suitable other herbicides comprising a carboxylic acid are pyridine herbicides comprising a carboxylic acid, such as fluroxypyr, triclopyr; triazolopyrimidine herbicides comprising a carboxylic acid, such as cloransulam; pyrimidinylsulfonylurea herbicides comprising a carboxylic acid, such as bensulfuron, chlorimuron, foramsulfuron, halosulfuron, mesosulfuron, primisulfuron, sulfometuron; imidazolinone herbicides, such as imazamethabenz, imazamethabenz, imazamox, imazapic, imazapyr, imazaquin and imazethapyr; triazolinone herbicides such as flucarbazone, propoxycarbazone and thiencarbazone; aromatic herbicides such as acifluorfen, bifenox, carfentrazone, flufenpyr, flumiclorac, fluoroglycofen, fluthiacet, lactofen, pyraflufen. Further on, chlorflurenol, dalapon, endothal, flamprop, flamprop-M, flupropanate, flurenol, oleic acid, pelargonic acid, TCA may be mentioned as other herbicides comprising a carboxylic acid.

Suitable anionic pesticides are fungicides, which comprise a carboxylic, thiocarbonic, sulfonic, sulfinic, thiosulfonic or phosphorous acid group, especially a carboxylic acid group. Examples are polyoxin fungicides, such as polyoxorim.

Suitable anionic pesticides are insecticides, which comprise a carboxylic, thiocarbonic, sulfonic, sulfinic, thiosulfonic or phosphorous acid group, especially a carboxylic acid group. Examples are thuringiensin.

Suitable anionic pesticides are plant growth regulators, which comprise a carboxylic, thiocarbonic, sulfonic, sulfinic, thiosulfonic or phosphorous acid group, especially a carboxylic acid group. Examples are 1-naphthylacetic acid, (2-naphthyloxy)acetic acid, indol-3-ylacetic acid, 4-indol-3-ylbutyric acid, glyphosine, jasmonic acid, 2,3,5-triiodobenzoic acid, prohexadione, trinexapac, preferably prohexadione and trinexapac.

Preferred anionic pesticides are anionic herbicides, more preferably dicamba, glyphosate, 2,4-D, aminopyralid, aminocyclopyrachlor and MCPA. Especially preferred are dicamba and glyphosate. In another preferred embodiment, dicamba is preferred. In another preferred embodiment, 2,4-D is preferred. In another preferred embodiment, glyphosate is preferred. In another preferred embodiment, MCPA is preferred.

In another preferred form the pesticide comprises an auxin herbicide. Various synthetic and natural auxin herbicides are known, wherein synthetic auxin herbicides are preferred. Preferably, the auxin herbicide comprises a protonizable hydrogen. More preferably, auxin herbicides relate to pesticides comprising a carboxylic, thiocarbonic, sulfonic, sulfinic, thiosulfonic or phosphorous acid group, especially a carboxylic acid group. The aforementioned groups may be partly present in neutral form including the protonizable hydrogen. Examples for natural auxin herbicides are indole-3acetic acid (IAA), phenyl acetic acid (PAA), 4-chloroindole-3-acetic acid (4-CI-IAA), and indole-3-butanoic acid (IBA). Examples for synthetic auxin herbicides are 2,4-D and its salts, 2,4-DB and its salts, aminopyralid and its salts such as aminopyralid-tris(2-hydroxypropyl)ammonium, benazolin, chloramben and its salts, clomeprop, clopyralid and its salts, dicamba and its, dichlorprop and its salts, dichlorprop-P and its salts, fluroxypyr, MCPA and its salts, MCPA-thioethyl, MCPB and its salts, mecoprop and its salts, mecoprop-P and its salts, picloram and its salts, quinclorac, quinmerac, TBA (2,3,6) and its salts, triclopyr and its salts, and aminocyclopyrachlor and its salts. Preferred auxin herbicides are 2,4-D and its salts, and dicamba and its salts, wherein dicamba is more preferred. In another more preferred form, the auxin herbicide contains an alkali metal salt of dicamba, such as sodium and/or potassium. Mixtures of the aforementioned auxin herbicides are also possible.

In a particular preferred form the pesticide formulation comprises dicamba, glyphosate or a mixture thereof.

Dicamba is a known herbicide, which may be present in form of an protonated acid, in form of a salt, or a mixture thereof. Various dicamba salts may be used, such as dicamba sodium, dicamba dimethylamine, dicamba diglyclolamine. Preferably, dicamba is present in form of a dicamba polyamine salt and the polyamine has the formula (A1)

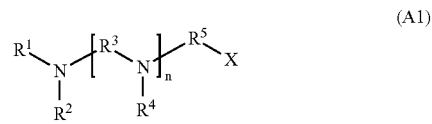

(A1)

wherein $R^1$, $R^2$, $R^4$, $R^6$, and $R^7$ are independently H or $C_1$-$C_6$-alkyl, which is optionally substituted with OH,
$R^3$ and $R^5$ are independently $C_2$-$C_{10}$-alkylene,
X is OH or $NR^6R^7$, and
n is from 1 to 20;
or the formula (A2)

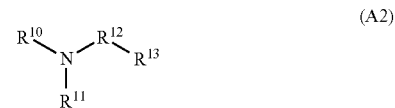

(A2)

wherein $R^{10}$ and $R^{11}$ are independently H or $C_1$-$C_6$-alkyl,
$R^{12}$ is $C_1$-$C_{12}$-alkylene, and
$R^{13}$ is an aliphatic $C_5$-$C_8$ ring system, which comprises either nitrogen in the ring or which is substituted with at least one unit $NR^{10}R^{11}$.

The term "polyamine" within the meaning of the invention relates to an organic compound comprising at least two amino groups, such as an primary, secondary or tertiary amino group.

The dicamba polyamine salt usually comprises an anionic dicamba and a cationic polyamine. The term "cationic polyamine" refers to a polyamine, which is present as cation. Preferably, in a cationic polyamine at least one amino group is present in the cationic form of an ammonium, such as R—N$^+$H$_3$, R$_2$—N$^+$H$_2$, or R$_3$—N$^+$H. An expert is aware which of the amine groups in the cationic polyamine is preferably protonated, because this depends for example on the pH or the physical form. In aqueous solutions the alkalinity of the amino groups of the cationic polyamine increases usually from tertiary amine to primary amine to secondary amine.

In an embodiment the cationic polyamine has the formula

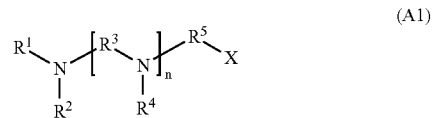

(A1)

wherein $R^1$, $R^2$, $R^4$, $R^6$, $R^7$ are independently H or $C_1$-$C_6$-alkyl, which is optionally substituted with OH, $R^3$ and $R^5$ are independently $C_2$-$C_{10}$-alkylene, X is OH or $NR^6R^7$, and n is from 1 to 20. $R^1$, $R^2$, $R^4$, $R^6$ and $R^7$ are preferably independently H or methyl. Preferably, $R^1$, $R^2$, $R^6$ and $R^7$ are H. $R^6$ and $R^7$ are preferably identical to $R^1$ and $R^2$, respectively. $R^3$ and $R^5$ are preferably independently $C_2$-$C_3$-alkylene, such as ethylene (—$CH_2CH_2$—), or n-propylene (—$CH_2CH_2CH_2$—). Typically, $R^3$ and $R^5$ are identical. $R^3$ and $R^5$ may be linear or branched, unsubstituted or substituted with halogen. Preferably, $R^3$ and $R^5$ are linear. Preferably, $R^3$ and $R^5$ are unsubstituted. X is preferably $NR^6R^7$. Preferably, n is from 1 to 10, more preferably from 1 to 6, especially from 1 to 4. In another preferred embodiment, n is from 2 to 10. Preferably, $R^1$, $R^2$, and $R^4$ are independently H or methyl, $R^3$ and $R^5$ are independently $C_2$-$C_3$-alkylene, X is OH or $NR^6R^7$, and n is from 1 to 10.

The group X is bound to $R^5$, which is a $C_2$-$C_{10}$-alkylene group. This means that X may be bound to any carbon atom of the $C_2$-$C_{10}$-alkylene group. Examples of a unit —$R^5$—X are —$CH_2$—$CH_2$—$CH_2$—OH or —$CH_2$—CH(OH)—$CH_3$.

$R^1$, $R^2$, $R^4$, $R^6$, $R^7$ are independently H or $C_1$-$C_6$-alkyl, which is optionally substituted with OH. An example such a substitution is formula (B1.9), in which $R^4$ is H or $C_1$-$C_6$-alkyl substituted with OH (more specifically, $R^4$ is $C_3$-alkyl substituted with OH. Preferably, $R^1$, $R^2$, $R^4$, $R^6$, $R^7$ are independently H or $C_1$-$C_6$-alkyl.

In another preferred embodiment the cationic polymer of the formula (A1) is free of ether groups (—O—). Ether groups are known to enhance photochemical degradation resulting in explosive radicals or peroxy groups.

Examples for cationic polyamines of the formula (A1) wherein X is $NR^6R^7$ are diethylenetriamine (DETA, (A4) with k=1, corresponding to (A1.1)), triethylenetetraamine (TETA, (A4) with k=2), tetraethylenepentaamine (TEPA, (A4) with k=3). Technical qualities of TETA are often mixtures comprising in addition to linear TETA as main component also tris-aminoethylamine TAEA, Piperazinoethylethylenediamine PEEDA and Diaminoethylpiperazine DAEP. Technical qualities of TEPA a are often mixtures comprising in addition to linear TEPA as main component also aminoethyltris-aminoethylamine AE-TAEA, aminoethyldiaminoethylpiperazine AE-DAEP and aminoethylpiperazinoethylethylenediamine AE-PEEDA. Such ethyleneamines are commercially available from Dow Chemical Company. Further examples are Pentamethyldiethylenetriamine PMDETA (B1.3), N,N,N',N'',N''-pentamethyl-dipropylenetriamine (B1.4) (commercially available as Jeffcat® ZR-40), N,N-bis(3-dimethylaminopropyl)-N-isopropanolamine (commercially available as Jeffcat® ZR-50), N'-(3-(dimethylamino)propyl)-N,N-dimethyl-1,3-propanediamine (A1.5) (commercially available as Jeffcat® Z-130), and N,N-Bis(3-aminopropyl)methylamine BAPMA (A1.2). Especially preferred are (A4), wherein k is from 1 to 10, (A1.2), (A1.4) and (A1.5). Most preferred are (A4), wherein k is 1, 2, 3, or 4 and (A1.2). In particular preferred are (A1.1) and (A1.2), wherein the latter is most preferred.

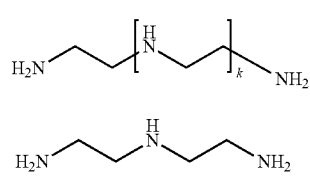
(A4)

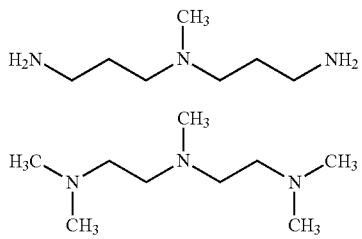
(A1.1)

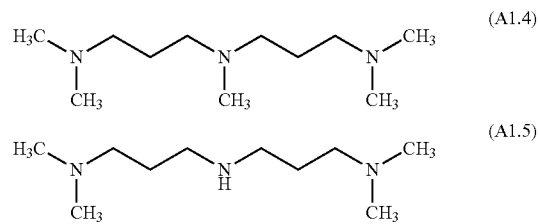
(A1.2)

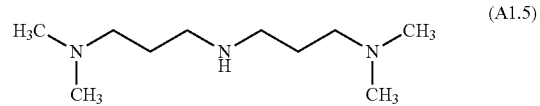
(A1.3)

(A1.4)

(A1.5)

Examples for polyamines of the formula (A1) wherein X is OH are N-(3-dimethylaminopropyl)-N,N-diisopropanolamine DPA (A1.9), N,N,N'-trimethylaminoethyl-ethanolamine (A1.7) (commercially available as Jeffcat® Z-110), aminopropylmonomethylethanolamine APMMEA (A1.8), and aminoethylethanolamine AEEA (A1.6). Especially preferred is (A1.6).

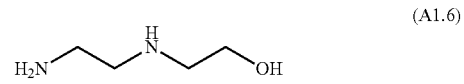
(A1.6)

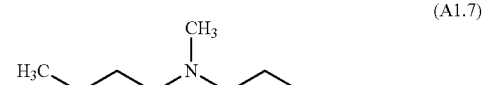
(A1.7)

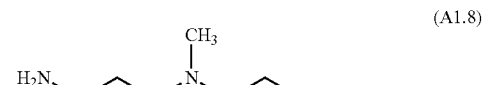
(A1.8)

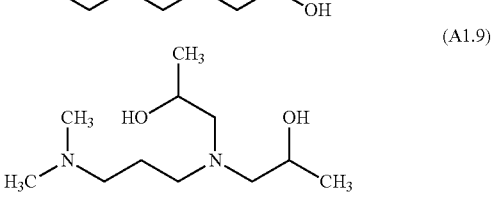
(A1.9)

In another embodiment the cationic polyamine has the formula

(A2)

wherein $R^{10}$ and $R^{11}$ are independently H or $C_1$-$C_6$-alkyl, $R^{12}$ is $C_2$-$C_{12}$-alkylene, and $R^{13}$ is an aliphatic $C_5$-$C_8$ ring system, which comprises either nitrogen in the ring or which is substituted with at least one unit $NR^{10}R^{11}$.

$R^{10}$ and $R^{11}$ are preferably independently H or methyl, more preferably H. Typically $R^{10}$ and $R^{11}$ are linear or branched, unsubstituted or substituted with halogen. Preferably, $R^{10}$ and $R^{11}$ are unsubstituted and linear. More preferably, $R^{10}$ and $R^{11}$ are identical.

$R^{12}$ is preferably $C_2$-$C_4$-alkylene, such as ethylene (—$CH_2CH_2$—), or n-propylene (—$CH_2CH_2CH_2$—). $R^{12}$ may be linear or branched, preferably it is linear. $R^{12}$ may be unsubstituted or substituted with halogen, preferably it is unsubstituted.

$R^{13}$ is an aliphatic $C_5$-$C_8$ ring system, which comprises either nitrogen in the ring or which is substituted with at least one unit $NR^{10}R^{11}$. Preferably, $R^{13}$ is an aliphatic $C_5$-$C_8$ ring system, which comprises nitrogen in the ring. The $C_5$-$C_8$ ring system may be unsubstituted or substituted with at least one $C_1$-$C_6$ alkyl group or at least one halogen. Preferably, the $C_5$-$C_8$ ring system is unsubstituted or substituted with at least one $C_1$-$C_4$ alkyl group. Examples for an aliphatic $C_5$-$C_8$ ring system, which comprises nitrogen in the ring, are piperazyl groups. Examples for $R^{13}$ being an aliphatic $C_5$-$C_8$ ring system, which comprises nitrogen in the ring, are the compounds of the formula (A2.11) and (A2.12) below. Examples for $R^{13}$ being an aliphatic $C_5$-$C_8$ ring system, which is substituted with at least one unit $NR^{10}R^{11}$ is the compound of the formula (A2.10) below.

More preferably, $R^{10}$ and $R^{11}$ are independently H or methyl, $R^{12}$ is $C_2$-$C_3$-alkylene, and $R^{13}$ is an aliphatic $C_5$-$C_8$ ring system, which comprises oxygen or nitrogen in the ring. In another preferred embodiment the cationic polymer of the formula (A2) is free of ether groups (—O—).

Especially preferred cationic polyamines of formula (A2) are isophorone diamine ISPA (A2.10), aminoethylpiperazine AEP (A2.11), and 1-methyl-4-(2-dimethylaminoethyl)piperazine TAP (A2.12). These compounds are commercially available from Huntsman or Dow, USA. Preferred are (A2.10) and (A2.11), more preferably (A2.11). In another embodiment (A2.11) and (A2.12) are preferred.

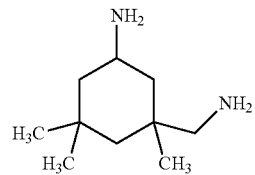

(A2.10)

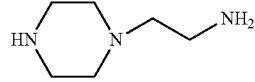

(A2.11)

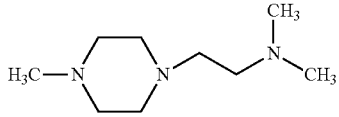

(A2.12)

Dicamba is most preferred present in form of a N,N-bis (3-aminopropyl)methylamine (so called "BAPMA") salt.

The pesticide formulation contains usually at least 50 g/l, preferably at least 300 g/l, more preferably at least 400 g/l, and in particular at least 450 g/l acid equivalents (AE) of dicamba. The pesticide formulation contains usually up to 800 g/l, preferably up to 700 g/l, more preferably up to 650 g/l, and in particular up to 600 g/l acid equivalents (AE) of dicamba.

The pesticide formulation according to the invention is usually present in form of an homogenous solution, e.g. at 20° C.

The invention also relates to a method of controlling phytopathogenic fungi and/or undesired vegetation and/or undesired insect or mite attack and/or for regulating the growth of plants, wherein the tank mix or the pesticide formulation is allowed to act on the respective pests, their environment or the plants to be protected from the respective pest, on the soil and/or on undesired plants and/or the crop plants and/or their environment.

Examples of suitable crops and plants to be protected are the following: *Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Brassica juncea, Brassica campestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *prunus domestica, Ribes sylvestre, Ricinus communis, Saccharum officinarum, Secale cereale, Sinapis alba, Solanum tuberosum, Sorghum bicolor* (s. *vulgare), Theobroma cacao, Trifolium pratense, Triticum aestivum, Triticale, Triticum durum, Vicia faba, Vitis vinifera, Zea mays.*

Preferred crops are: *Arachis hypogaea, Beta vulgaris* spec. *altissima, Brassica napus* var. *napus, Brassica oleracea, Brassica juncea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus* spec., *Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor* (s. *vulgare), Triticale, Triticum aestivum, Triticum durum, Vicia faba, Vitis vinifera* and *Zea mays.*

The method according to the invention can preferably be used in genetically modified crops. The term "genetically modified crops" is to be understood as plants, which genetic material has been modified by the use of recombinant DNA techniques in a way that under natural circumstances it cannot readily be obtained by cross breeding, mutations, natural recombination, breeding, mutagenesis, or genetic engineering. Typically, one or more genes have been integrated into the genetic material of a genetically modified plant in order to improve certain properties of the plant. Such genetic modifications also include but are not limited to targeted post-transitional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, are particularly useful with the composition and method according to the invention. Tolerance to classes of herbicides has been developed such as auxin herbicides such as dicamba or 2,4-D (i.e. auxin tolerant crops); bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase (PPO) inhibitors; lipid biosynthesis inhibitors such as acetyl CoA carboxylase (ACCase) inhibitors; or oxynil (i.e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Examples of these herbicide resistance technologies are also described in US 2008/0028482, US2009/0029891, WO 2007/143690, WO 2010/080829, U.S. Pat. No. 6,307, 129, U.S. Pat. No. 7,022,896, US 2008/0015110, U.S. Pat. No. 7,632,985, U.S. Pat. No. 7,105,724, and U.S. Pat. No. 7,381,861, each herein incorporated by reference.

Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox, or ExpressSun® sunflowers (DuPont, USA) being tolerant to sulfonyl ureas, e.g. tribenuron. Genetic engineering methods have been used to render cultivated plants such as soybean, cotton, corn, beets and rape, tolerant to herbicides such as glyphosate, dicamba, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Preferably, the crops are genetically modified crops, that are tolerant at least to auxins, in particular crops which are tolerant at least to dicamba or 2,4-D. In a preferred form the crops are tolerant to auxins (e.g. dicamba or 2,4-D) and to glyphosate.

Furthermore, plants are also covered that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be under-stood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are dis-closed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal pro-teins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato culti-vars, which express resistance genes acting against *Phytophthora infestans* derived from the mexican wild potato *Solanum bulbocastanum*) or T4-lyso-zym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

Furthermore, it has been found that the composition and method according to the invention are also suitable for the defoliation and/or desiccation of plant parts, for which crop plants such as cotton, potato, oilseed rape, sunflower, soybean or field beans, in particular cotton, are suitable. In this regard compositions have been found for the desiccation and/or defoliation of plants, processes for preparing these compositions, and methods for desiccating and/or defoliating plants using the composition and method according to the invention.

As desiccants, the composition and method according to the invention are suitable in particular for desiccating the above-ground parts of crop plants such as potato, oilseed rape, sunflower and soybean, but also cereals. This makes possible the fully mechanical harvesting of these important crop plants.

Also of economic interest is the facilitation of harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the controlled defoliation of useful plants, in particular cotton. Moreover, a shortening of the time interval in which the individual cotton plants mature leads to an increased fiber quality after harvesting.

The composition and method according to the invention can be applied pre- or post-emergence, or together with the seed of a crop plant. It is also possible to apply the compounds and compositions by applying seed, pretreated with a composition of the invention, of a crop plant. If the active compounds A and C and, if appropriate C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

The term "growth stage" refers to the growth stages as defined by the BBCH Codes in "Growth stages of mono- and dicotyledonous plants", 2nd edition 2001, edited by Uwe Meier from the Federal Biological Research Centre for Agriculture and Forestry. The BBCH codes are a well established system for a uniform coding of phonologically similar growth stages of all mono- and dicotyledonous plant species. In some countries related codes are known for specific crops. Such codes may be correlated to the BBCH code as exemplified by Harell et al., Agronomy J. 1998, 90, 235-238.

The tank mix may be allowed to act on crops at any growth stage, such as at BBCH Code 0, 1, 2, 3, 4, 5, 6 and/or 7. Preferably, the tank mix is allowed to act on crops at a growth stage of BBCH Code 0, 1 and/or 2, or their habitat. In another preferred form, the tank mix is allowed to act on crops at a growth stage of BBCH Code 1, 2, 3, 4, 5, 6 and/or 7, especially 2, 3, 4, 5, 6 and/or 7.

The treatment of crop with a pesticide may be done by applying said pesticide by ground or aerial application, preferably by ground application. Suitable application devices are a predosage device, a knapsack sprayer, a spray tank or a spray plane. Preferably the treatment is done by ground application, for example by a predosage device, a knapsack sprayer or a spray tank. The ground application may be done by a user walking through the crop field or with a motor vehicle, preferably with a motor vehicle.

Usually, the tank mix is sprayed through a flat fan nozzle. Preferably, the tank mix is sprayed through an air induction flat fan nozzle (also called venture flat fan nozzle or injector flat fan nozzle). Such spray nozzles are commercially available, e.g. from Hypro LLC, Cambridge, Lechler, Germany, or agrotop, Germany.

The term "effective amount" denotes an amount of the tank mix, which is sufficient for controlling undesired vegetation and which does not result in a substantial damage to the treated crops. Such an amount can vary in a broad range and is dependent on various factors, such as the species to be controlled, the treated cultivated plant or habitat, the climatic conditions and the pesticide.

The tank mix is typically applied at a volume of 5 to 5000 l/ha, preferably of 50 to 500 l/ha. The tank mix is typically applied at a rate of 5 to 3000 g/ha pesticide (e.g. dicamba), preferably 20 to 1500 g/ha.

In a further embodiment, the composition or method according to the invention can be applied by treating seed. The treatment of seed comprises essentially all procedures familiar to the person skilled in the art (seed dressing, seed coating, seed dusting, seed soaking, seed film coating, seed multilayer coating, seed encrusting, seed dripping and seed pelleting) based on the composition and method according to the invention. Here, the herbicidal compositions can be applied diluted or undiluted.

The term seed comprises seed of all types, such as, for example, corns, seeds, fruits, tubers, seedlings and similar forms. Here, preferably, the term seed describes corns and seeds.

The seed used can be seed of the useful plants mentioned above, but also the seed of transgenic plants or plants obtained by customary breeding methods.

The rates of application of the active compound are from 0.0001 to 3.0, preferably 0.01 to 1.0 kg/ha of active substance (a.s.), depending on the control target, the season, the target plants and the growth stage. To treat the seed, the pesticides are generally employed in amounts of from 0.001 to 10 kg per 100 kg of seed.

The tank mix adjuvant usually contains at least 50 wt %, preferably at least 70 wt %, and in particular at least 90 wt % of the carbonate of the formula (I). In another preferred form the tank mix adjuvant consists of the carbonate of the formula (I). In a more preferred form the tank mix adjuvant contains at least 5 wt %, preferably at least 10 wt %, more preferably at least 15 and in particular at least 20 wt % of the carbonate of the formula (I).

The tank mix adjuvant is essentially free of pesticides. This means, that the tank mix adjuvant usually contains less than 5 wt %, preferably less than 1 wt %, more preferably less than 0.2 wt %, and in particular less than 0.05 wt % of a pesticide.

The tank mix adjuvant may be liquid or solid, preferably it is a liquid at 20° C. Preferably, the tank mix adjuvant is a homogenous liquid, which means that it consists of only one liquid phase.

The tank mix adjuvant may comprise further auxiliaries. Typically, the adjuvant contains up to 80 wt %, preferably up to 50 wt %, more preferably up to 20 wt % and in particular up to 3 wt % of further auxiliaries. In a preferred form, the adjuvant contains up to 98 wt %, preferably up to 95 wt %, more preferably up to 90 wt % and in particular up to 80 wt % of further auxiliaries. Examples for further auxiliaries are solvents, liquid carriers, surfactants, dispersants, emulsifiers, wetters, solubilizers, penetration enhancers, protective colloids, adhesion agents, thickeners, repellents, compatibilizers, bactericides, anti-freezing agents, anti-foaming agents, colorants.

The invention offers various advantages: There is a very low rate of unwanted phytotoxic damage to crops; the surface tension of a pesticidal formulation is decreased; the penetration of pesticides into to plant is enhanced; the pesticidal effect of the pesticide is increased; the tank mix adjuvants are easy and safe to handle and to apply; and the tank mix adjuvant may be incorporated in pesticide formulations; the pesticide formulation comprising the carbonate of the formula (I) is stable.

EXAMPLES

GECA: 4-Methoxycarbonyl-1,3-dioxolan-2-on; substance according to formula (I), wherein $R^a$ is methyl.
GECA-2: 1,2-Ethanediyl-bis(1,3-dioxolane-2-on-4-carboxylate); divalent substance according to formula (a).
BAPMA: N,N-Bis(3-aminopropyl)methylamine
Dicamba-K and Dicamba-BAPMA: Potassium salt and BAPMA salt of Dicamba, respectively.
GL-K: Glyphosate, potassium salt.

Example-1: Preparation of Dicamba Compositions

Compositions A-F were prepared containing the salts Dicamba-K or Dicamba-BAPMA according to Table 1. Herein, either the Dicamba-BAPMA or the free carbonic acid of Dicamba is premixed with water and the remaining ingredients are added as listed in Table 1.

TABLE 1

| Ingredient (mg/l) | A | B | C | D | E | F |
|---|---|---|---|---|---|---|
| Dicamba | 188 | 188 | 188 | — | — | — |
| Dicamba-BAPMA | — | — | — | 192 | 192 | 192 |
| KOH | 95 | 95 | 95 | — | — | — |
| GECA | — | 1840 | — | — | 1840 | — |
| GECA-2 | — | — | 1900 | — | — | 1900 |
| Water | To 1 L | To 1 L | To 1 L | To 1 L | To 1 L | To 1 L |

Example-2: Preparation of Glyphosate Compositions

Compositions G-L were produced as composition a A-F in Example-1, but additionally 370 mg of the potassium salt of glyphosate per liter were added. The ingredients are listed in Table 2.

TABLE 2

| Ingredient (mg/l) | G | H | I | J | K | L |
|---|---|---|---|---|---|---|
| Dicamba | 188 | 188 | 188 | — | — | — |
| Dicamba-BAPMA | — | — | — | 192 | 192 | 192 |
| KOH | 95 | 95 | 95 | — | — | — |
| GECA | — | 1840 | — | — | 1840 | — |
| GECA-2 | — | — | 1900 | — | — | 1900 |
| GL-K | 370 | 370 | 370 | 370 | 370 | 370 |
| Water | To 1 L | To 1 L | To 1 L | To 1 L | To 1 L | To 1 L |

Example-3: Reduction of the Surface Tension

The static surface tension of compositions A-F, H-I, K-L was tested by measuring the force on a Wilhelmy-plate. Hereby, the Wilhelmy plate consists of platinum that has been roughened on its surface to allow wetting by the sample. The plate is oriented perpendicular to the surface of the liquid and lowered until it contacts the sample. A thin film forms on both sides of the plate due to the surface tension of the liquid, causing a measurable pulling force on the plate. The mean values of three repetitive measurements are displayed in Table 3.

TABLE 3

| Composition | Ingredients | Static surface tension in mN/m ± variance $\sigma^2$ |
|---|---|---|
| A | Dicamba-K | 71.63 ± 0.0582 |
| B | Dicamba-K/GECA | 69.76 ± 0.0562 |
| C | Dicamba-K/GECA-2 | 56.52 ± 0.0631 |
| D | Dicamba-BAPMA | 72.35 ± 0.0976 |
| E | Dicamba-BAPMA/GECA | 70.20 ± 0.0612 |
| F | Dicamba-BAPMA/GECA-2 | 61.34 ± 0.0659 |
| H | Dicamba-K/GECA/GL-K | 68.35 ± 0.0816 |
| I | Dicamba-K/GECA-2/GL-K | 59.98 ± 0.0873 |
| K | Dicamba-BAPMA/GECA/GL-K | 69.90 ± 0.0869 |
| L | Dicamba-BAPMA/GECA-2/GL-K | 59.05 ± 0.0529 |
| Water | Distilled Water | 72.51 ± 0.0582 |

Upon addition of a carbonate according to formula (I), the static surface tension decreases in all samples compared to the blanks (water and compositions A/D).

Example-4: Penetration Enhancement of Pesticides in *Echinochloa Crus-Galli*

A volume of 1 µl of the compositions A (Dicamba-K), C (Dicamba-K, GECA-2) and I (Dicamba-K, GECA-2, GL-K) was applied on the surface of three plant leaves of *Echinochloa crus-galli* in triplicates. After drying, the plants were incubated for 3 h at 80% humidity at 20° C. Subsequently, the leaves' surface was washed with water to measure the remaining part of unpenetrated pesticide (Wash). The cuticula was analyzed by applying 50 µl of a solution of 5% cellulose acetate in acetone to the treated positions. After evaporation of the solvent, the cellulose acetate film was removed from the surface and extracted in acetone. The cellulose acetate was precipitated in petrol ether and the supernatant was analyzed (CA). Finally, the washed leaves were homogenized, extracted and the content of active ingredient was determined (Extract). All quantitative measurements were conducted with a UPLC-MS/MS device. Table 4 shows the mean results of these analyses as percentage of the Dicamba concentrations obtained with composition A.

TABLE 4

| Composition | Wash [%] | CA [%] | Extract [%] |
|---|---|---|---|
| A | 100 | 100 | 100 |
| B | 14 | 252 | 129 |
| C | 18 | 170 | 172 |

Samples B and C, both containing GECA-2, show an increased penetration (Extract) through the cuticula (CA) and a reduced wash-off (Wash) of the pesticide.

Example-5: Biological Efficacy Enhancement of Pesticidal Compositions

The adjuvant effect was tested in greenhouse trials on (a) *Echinochloa crus-galli, Chenopodium album* (b) and *Abutilon theophrasti* (c).

Plants (a), (b), and (c) were sprayed with compositions D, E*, F*, J, and L*, which were prepared according to Examples 1 and 2, but contained double the concentration of GECA in case of composition E* compared to composition E, and double the concentration of GECA-2 in case of F*, and L* compared to compositions F, and L.

Plants (a), and (b) were sprayed with compositions A, B*, C*, G, H*, and I*, which were prepared according to Examples 1 and 2, but contained double the concentration of GECA in case of compositions B*, and H*, compared to compositions B, and H, respectively, and double the concentration of GECA-2 in case of C*, and I*, compared to compositions C, and I, respectively. The herbicidal activity was evaluated 14 days after treatment by awarding scores to the treated plants in comparison to the untreated control plants (Tables 5 and 6). The evaluation scale ranges from 0% go 100% activity. 100% activity means the complete death of at least those parts of the plant that are above ground. Conversely, 0% activity means that there were no differences between treated and untreated plants. The effective concentration of Dicamba-BAPMA was 70 g/ha, the effective concentration of GL-K—if present—was 140 g/ha, the effective concentration of GECA, and GECA-2 was 1 L/ha. Herein, the effective concentration means the total mass of active ingredients per treated area.

The results displayed in Table 5 demonstrate the increased activity of the compositions E*, F* and L* compared to compositions D and J, which do not contain a carbonate compound.

The results displayed in Table 6 demonstrate the increased activity of the compositions B*, C*, H*, and I* compared to compositions A, and G, which do not contain a carbonate compound.

TABLE 5

| Herbicidal activity [%] of compositions D, E*, F*, J and L* on plant species (a)-(c) | | | |
|---|---|---|---|
| | (a) | (b) | (c) |
| D (Dicamba-BAPMA) | 0 | 23 | 45 |
| E* (Dicamba-BAPMA, GECA) | 27 | 33 | 57 |
| F* (Dicamba-BAPMA, GECA-2) | 45 | 85 | 67 |
| J (Dicamba-BAPMA, GL-K) | 50 | 30 | 43 |
| L* (Dicamba-BAPMA, GECA-2, GL-K) | 72 | 85 | 62 |

TABLE 6

| Herbicidal activity [%] of compositions A, B*, C* and G, H*, I* on plant species (a)-(b) | | |
|---|---|---|
| | (a) | (b) |
| A (Dicamba-K) | 15 | 62 |
| B* (Dicamba-K, GECA) | 43 | 80 |
| C* (Dicamba-K, GECA-2) | 25 | 85 |
| G (Dicamba-K, GL-K) | 43 | 62 |
| H* (Dicamba-K, GECA, GL-K) | 55 | 75 |
| I* (Dicamba-K, GECA-2, GL-K) | 65 | 92 |

We claim:

1. A pesticide formulation comprising a pesticide and a tank mix adjuvant which comprises a carbonate of the formula (I)

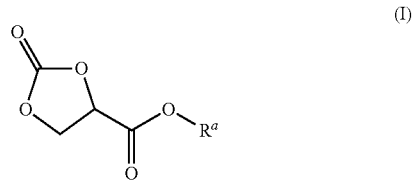

where $R^a$ is a $C_{1-12}$ alkyl, or a n-valent radical derived by abstraction of the OH groups of an n-valent polyol and which is substituted by n minus 1 carbonate groups of the formula (II)

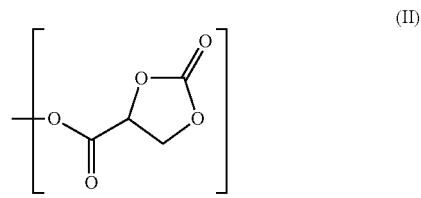

where n is from 2 to 4 and the polyol is an aliphatic polyol comprising 2 to 10 carbon atoms;
wherein the tank mix adjuvant contains less than 5 wt % of pesticides.

2. The formulation of claim 1, wherein the pesticide is present in dissolved form.

3. The formulation of claim 1, in form of a liquid.

4. The formulation of claim 1, wherein the weight ratio of the pesticide to the carbonate of the formula (I) is from 1:1 to 1:100.

5. The formulation of claim 1, wherein $R^a$ is a linear, or branched $C_{1-10}$ alkyl or the index n is 2 or 3 and the polyol is an aliphatic polyol comprising 2 to 8 carbon atoms.

6. The formulation of claim 1, wherein $R^a$ is methyl, ethyl, n-butyl, iso-butyl, n-hexyl, branched octyl, branched decyl, or n is 2, the polyol is 1,2-ethanediol, 1,4-butanediol or 2,2-dimethyl-1,3-propanediol.

7. A method of controlling phytopathogenic fungi, and/or undesired vegetation, and/or undesired insect or mite attack, and/or for regulating the growth of plants, the formulation of claim 1, or a tank mix comprising the formulation, is allowed to act on the respective pests, their environment or the plants to be protected from the respective pest, on the soil, and/or on undesired plants, and/or the crop plants, and/or their environment.

8. The method of claim 7, wherein the pesticide is present in dissolved form.

9. The method of claim 7, in form of a liquid.

10. The method of claim 7, wherein the weight ratio of the pesticide to the carbonate of the formula (I) is from 1:1 to 1:100.

11. The method of claim 10, wherein $R^a$ is a linear, or branched $C_{1-10}$ alkyl, or the index n is 2 or 3 and the polyol is an aliphatic polyol comprising 2 to 8 carbon atoms.

12. The method of claim 11, wherein $R^a$ is methyl, ethyl, n-butyl, iso-butyl, n-hexyl, branched octyl, branched decyl, or n is 2, the polyol is 1,2-ethanediol, 1,4-butanediol or 2,2-dimethyl-1,3-propanediol.

* * * * *